US00PP10041P

United States Patent [19]

Glicenstein

[11] Patent Number: Plant 10,041

[45] Date of Patent: Sep. 23, 1997

[54] CHRYSANTHEMUM PLANT NAMED 'GENTLE KIMBERLY'

[75] Inventor: Leon Glicenstein, Salinas, Calif.

[73] Assignee: Yoder Brothers, Inc., Barberton, Ohio

[21] Appl. No.: 605,812

[22] Filed: Feb. 22, 1996

[51] Int. Cl.[6] ..... A01H 5/00

[52] U.S. Cl. ..... Plt./82.3

[58] Field of Search ..... Plt./74.1, 82.3, Plt./82.4

[56] References Cited

U.S. PATENT DOCUMENTS

P.P. 9,026 1/1995 VandenBerg ..... Plt./82.4
4,616,099 10/1986 Sparkes ..... 47/58

OTHER PUBLICATIONS

Broertjes, et al., 1980, "A Mutant of a Mutant of a . . . Irradiation of Progressive Radiation–Induced Mutants in a Mutation Breeding Programme with *Chrysanthemum morifolium*", Euphytica, 29:525–530.

Gosling, ed., 1979, "The Chrysanthemum Manual—6th Edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and Rose Mutations Induced by X–Rays", Am. Soc. Hort. Sci. Proc., pp. 613–620.

Broertjes, 1966, "Mutation Breeding of Chrysanthemums", Euphytica, 15:156–162.

Dowrick, et al., 1966, "The Induction of Mutations in Chrysanthemum Using X–and Gamma Radiation", Euphytica, 15:204–210.

*Primary Examiner*—Howard J. Locker
*Attorney, Agent, or Firm*—Foley & Lardner

[57] ABSTRACT

A Chrysanthemum plant named Gentle Kimberly particularly characterized by its flat capitulum form; daisy capitulum type; greyed-orange ray floret color; diameter across face of capitulum of 47 to 52 mm when fully opened; branching pattern is spreading and prolific, with 9 laterals developing after pinch when grown outside under natural daylength in fall flowerings; natural season flower date of September 2 to 7 when planting rooted cuttings on June 17 to 21 in Salinas, Calif., and of October 5 to 17 when planting rooted cuttings June 15 to 18 in Hightstown, N.J.; plant height of 30 to 36 cm when grown in fall under natural daylength with no growth regulators; and durable, uniform performance.

1 Drawing Sheet

The present invention comprises a new and distinct cultivar of Chrysanthemum, botanically known as *Dendranthema grandiflora*, and referred to by the cultivar name Gentle Kimberly.

Gentle Kimberly, identified as 7998 (89-707G02), is a product of a mutation induction program. The new cultivar was discovered and selected by inventor Leon Glicenstein on Sep. 1, 1993 in a controlled environment in Salinas, Calif. as one flowering plant within a flowering block established as rooted cuttings from stock plants which had been exposed as unrooted cuttings to an X-ray source of 1500 rads in Fort Myers, Fla. on Feb. 25, 1993. The irradiated parent cultivar was the cultivar Kimberly, disclosed in U.S. Plant Pat. No. 9,026 and described as a flat daisy garden mum with light purple flower color.

The irradiation program resulting in Gentle Kimberly had as its primary objective the expansion of color ranges of the parent cultivar Kimberly. The irradiation program comprised irradiation of cuttings of the parent cultivar at irradiation levels of 1500, 1750 and 2000 rads. A total of 986 cuttings harvested from a total of 225 irradiated plants were planted on Jun. 21, 1993. Of these, 13 initial selections were made, which selections were then revegetated and reflowered. Three consecutive flowerings resulted in discarding 6 of the original 13 selections on Apr. 18, 1994. The remaining 7 selections were maintained as PIs (Possible Introductions) and further trialed in Salinas, Calif., Hightstown, N.J. and Leamington, Ontario, Canada, ultimately resulting discarding 5 selections on Oct. 17, 1994, and the decision to introduce one selection as Gentle Kimberly, and the other selection as Autumn Kimberly, disclosed in a pending application Ser. No. 08/605,819.

The first act of asexual reproduction of Gentle Kimberly was accomplished when vegetative cuttings were taken from the initial selection in November of 1993 in a controlled environment in Salinas, Calif., by technicians working under supervision of Leon Glicenstein.

Horticultural examination of controlled flowerings of successive plantings has shown that the unique combination of characteristics as herein disclosed for Gentle Kimberly are firmly fixed and are retained through successive generations of asexual reproduction.

Gentle Kimberly has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Gentle Kimberly, which, in combination, distinguish this Chrysanthemum as a new and distinct cultivar:

1. Flat capitulum form.
2. Daisy capitulum type.
3. Greyed-orange ray floret color.
4. Diameter across face of capitulum of 47 to 52 mm when fully opened.
5. Branching pattern is spreading and prolific, with 9 laterals developing after pinch when grown outside under natural daylength in fall flowerings.

6. Natural season flower date of September 2 to 7 when planting rooted cuttings on June 17 to 21 in Salinas, Calif., and of October 5 to 17 when planting rooted cuttings June 15 to 18 in Hightstown, N.J.

7. Plant height of 30 to 36 cm when grown in fall under natural daylength with no growth regulators.

8. Durable, uniform performance.

The accompanying photographic drawing is a color photograph of Gentle Kimberly grown as a pinched garden mum under natural season outside conditions in Leamington, Ontario, Canada, with the colors being as nearly true as possible with illustrations of this type. Plants were grown outside in 8"×5" pots and shipped to Salinas, Calif. for photography purposes.

Of the commercial cultivars known to the inventor, the most similar in comparison to Gentle Kimberly is the parent cultivar Kimberly. All traits of Gentle Kimberly are similar to those of Kimberly, except for the ray floret color. The ray floret color of Gentle Kimberly is greyed-orange (R.H.S. 168A to 168C), while the ray floret color of Kimberly is light purple (R.H.S. 75B to 75C) Gentle Kimberly similarly differs from sibling cultivar Autumn Kimberly only with respect to ray floret color.

In the following description color references are made to The Royal Horticultural Society Colour Chart. The color values were determined on plant material grown as a pinched garden mum grown outdoors in Salinas, Calif. on Sep. 1, 1995.

Classification:

*Botanical.*—*Dendranthema grandiflora* cv Gentle Kimberly.

*Commercial.*—Flat daisy garden mum.

INFLORESCENCE

A. Capitulum:

*Form.*—Flat.

*Type.*—Daisy.

*Diameter across face.*—7 to 52 mm when fully opened.

B. Corolla of ray florets:

*Color (general tonality from a distance of three meters)* .—Greyed-orange.

*Color (upper surface).*—168A to 168C.

*Color (under surface).*—168C to 168D.

*Shape.*—Cross-section flat, longitudinal section straight. Ray floret tips rounded.

C. Corolla of disc florets:

*Color (mature).*—17C.

*Color (immature).*—14A, tinged with 144C.

D. Reproductive organs:

*Androecium.*—Present on disc florets only; moderate pollen.

*Gynoecium.*—Present on both ray and disc florets.

PLANT

A. General appearance:

*Height.*—30 to 36 cm when grown in fall under natural daylength with no growth regulators.

*Branching pattern.*—Spreading and prolific, with 9 laterals developing after pinch when grown outside under natural daylength in fall flowerings.

B. Foliage:

*Color (upper surface).*—147A.

*Color (under surface).*—147B.

*Shape.*—Small, lobed, slightly serrated.

What is claimed is:

1. A new and distinct Chrysanthemum plant named Gentle Kimberly, as described and illustrated.

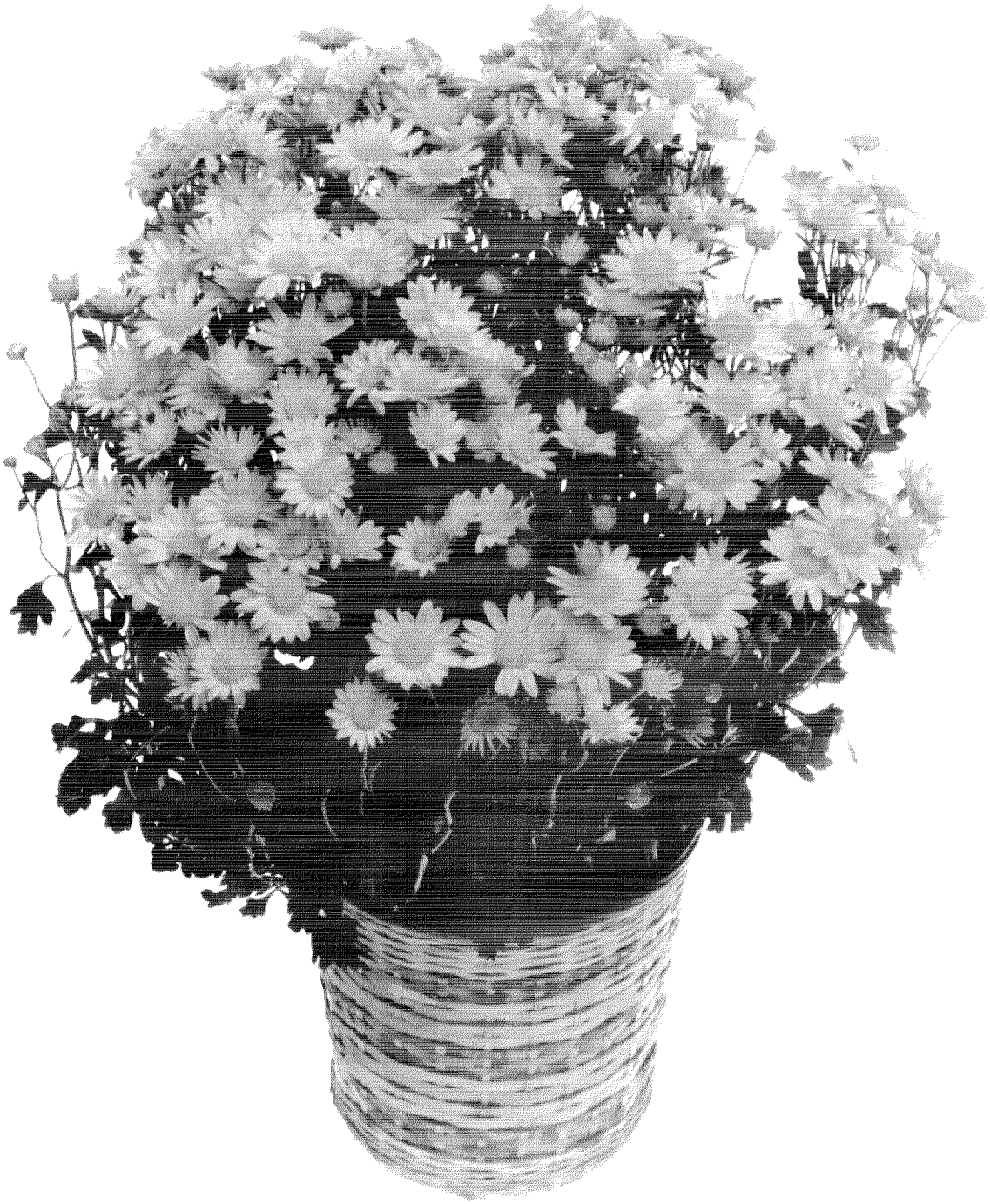

* * * * *